United States Patent [19]

Samelson

[11] 4,169,473

[45] Oct. 2, 1979

[54] ANTI-SNORING AND ANTI-BRUXISM DEVICE

[76] Inventor: Charles F. Samelson, 5712 S. Kenwood, Chicago, Ill. 60637

[21] Appl. No.: 883,270

[22] Filed: Mar. 3, 1978

[51] Int. Cl.$^2$ .............................................. A61F 5/56
[52] U.S. Cl. .................................. 128/136; 128/132 R
[58] Field of Search ................... 128/136, 137, 138 R, 128/132 R, 208, 147, 15

[56] References Cited

U.S. PATENT DOCUMENTS 3,211,143  10/1965  Grossberg ........................... 128/136

FOREIGN PATENT DOCUMENTS 65194  11/1892  Fed. Rep. of Germany ........... 128/136
2704709  8/1977  Fed. Rep. of Germany ........... 128/136

*Primary Examiner*—Henry J. Recla
*Attorney, Agent, or Firm*—Norman Lettvin

[57] ABSTRACT

A device is provided for positioning within the mouth of a user for preventing snoring and nocturnal tooth grinding. The device is an integrally molded body providing an externally located lip-engaging member and internally located parts to be positioned within the user's mouth. The internal portion of the device provides dental engaging arches and a rearwardly-opening central socket for cooperating with the forward portion of the user's tongue in a manner to draw the tongue forwardly so as to increase the unobstructed dimension of the nasal breathing passage. When operatively positioned within the mouth, at least one set of the user's upper or lower dental arches will enter into a channel provided by the device. The device substantially eliminates oral breathing. The tongue will be held in the socket by a negative pressure developed in the socket. When the tongue is held, it draws the body of the tongue forwardly of its usual restive position behind the lower teeth and adjacent the soft palate, the uvula and the posterior pharyngeal wall, thereby increasing the dimension of the air flow passage through the nasopharynx to facilitate nasal breathing. The device's engagement with at least one of the user's dental arches operates to eliminate nocturnal tooth-grinding.

7 Claims, 4 Drawing Figures

ANTI-SNORING AND ANTI-BRUXISM DEVICE

FIELD OF THE INVENTION

This invention relates to an anti-snore and anti-tooth-grinding device, and more particularly, to a device for selective insertion within the mouth of a user so as to obstruct the oral flow of air past the lips of the user, and to increase the size of the air passageway through the oro- and naso-pharynx, and which may also be provided with means for immobilizing jaw movement.

BACKGROUND OF THE INVENTION

Snoring is caused by the relaxation of body tissue in the lingual compartment, the tissue including the tongue, the pharyngeal folds, the soft palate, the muscularis uvulae and the palate-pharyngeal arch. During normal waking hours, muscle tone in most individuals unconsciously maintains the above structures in adequate spacial relationships so as not to interfere with the free passage of air therepast. However, with increasing age, and during periods of unconsciousness, some muscle tone is lost, thereby allowing one or more of the tongue, the pharyngeal folds, the soft palate, the uvulae and the posterior pharyngeal wall to vibrate as tidal air flows therepast.

While the act of snoring is socially discomfitting to other persons who hear the snores, and especially annoying to a spouse attempting to sleep, it can also cause harmful complications to the snorer, such as disturbed rest, excessive drying of the oro- and naso-pharyngeal mucous membranes with consequent injury to the throat, middle and inner ear, susceptibility to infection, vertigo and impaired hearing. Of equal importance is the fact that people who snore are not making use of the physiologically beneficial aspects of nasal breathing. The anatomical nasal structures, (such as the turbinates, mucous membranes, etc.) provide moistening and cleansing functions during sleep.

Prior patents, such as U.S. Pat. No. 3,132,647, have dealt with the various lingual compartment tissues and their relationship to the snoring phenomenon. Such patents disclose that snoring should and can be reduced, if not altogether prevented, by providing for unobstructed air flow between the tongue and the soft palate. U.S. Pat. No. 3,132,647 seeks to keep the passage open by engaging and depressing the rear portion of the tongue while supporting a portion of the downwardly-hanging soft palate. Oral breathing is permitted, and no attempt is made to prevent vibration of the forward end of the tongue.

Other patented devices have been proposed as "snore-preventing" such as U.S. Pat. Nos. 1,774,446 and 3,434,470, and British Pat. No. 1,248,474. All such prior proposals have been constructed to permit, or at least allow, the partial inhalation of air orally to insure that oral breathing occurred.

While U.S. Pat. No. 2,867,212 recognizes that snoring is caused by vibrations of the soft palate and uvula and could be prevented if oral breathing is prevented, the mouthpiece described in said patent is intended to serve as an aid for practice of nasal breathing by blocking the oral flow of air. No attempt is made in said device to open the naso-pharynx, thus presenting a troublesome situation for users whose muscle tone is such as to partially close the nasal passageway.

British Pat. No. 751,381 includes a device to be held within the mouth of a user, said device having a central open bore provided for continuous passage of air.

It is one object of the present invention to provide an anti-snore device which serves to receive and hold the forward portion of the tongue in a forward position, thereby drawing the remainder of the tongue forwardly and in such a way that no portion of the tongue, or other oral soft tissue, will vibrate during breathing.

It is a further object of the present invention to provide an anti-snore device which not only holds the forward portion of the tongue forwardly but also prevents oral breathing by obstructing the flow of air through the mouth.

It is another object of this invention to provide an anti-snore device which not only prevents oral breathing, but also, opens the internal air passageway for nasal breathing through the naso-pharynx.

A still further object of the present invention is to provide an anti-snore device which prevents oral breathing by obstructing the flow of air through the mouth, holds the tongue forwardly so as to prevent soft tissue vibration, and opens the air passageway for nasal breathing.

And still another object of this invention is to provide a novel combination anti-snore and anti-bruxism device.

These and other objects and advantages of the invention will become clear from the following description of a preferred embodiment of the invention.

BRIEF SUMMARY OF THE INVENTION

The anti-snore and anti-bruxism device of this invention is adapted for partial insertion into the mouth of a user with means for obstructing the oral flow of air and for holding the tongue forwardly, thereby preventing oral breathing and enlarging the internal naso-pharynx to enhance nasal breathing. The device includes a forward molded body portion of a size to cover the user's mouth and lips, and another portion for entry into the mouth to engage at least one of the user's upper or lower teeth or gum arches to hold the device in position and to prevent the passage of air therepast. A tongue-receiving socket with a closed forward end extends rearwardly from and is attached to the body portion, the rear end of the socket being open and sized and shaped to receive a part of the forward end of the user's tongue. When operatively positioned within the mouth, the user creates a negative pressure within the socket by applying gentle suction, thereby effecting a holding by the socket of a portion of the tongue within the socket. The position of the tongue, when so secured, is to be pulled forwardly of its normal resting position behind the lower teeth. The remainder of the body of the tongue, when held forwardly of its normal proximity to the soft palate, the uvula and the posterior pharyngeal wall, provides an increase in size of the nasal air passageway. Because the device is molded for removable cooperation with the upper and lower dental arches, relative jaw movement is effectively precluded, and nocturnal tooth grinding is prevented.

DETAILED DESCRIPTION OF THE INVENTION

Figure 1:
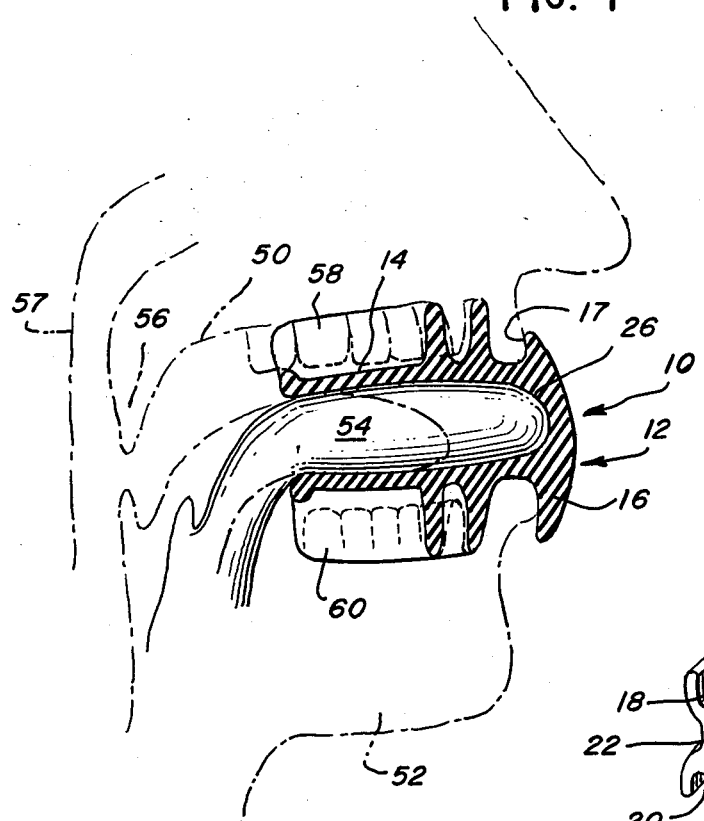
FIG. 1 is a vertical, cross-sectional view, along the longitudinal axis, or line 1—1 of FIG. 2, of the anti-snoring and anti-bruxism device of the present invention, illustrating the device operatively positioned in the mouth of a user.
Figure 2:
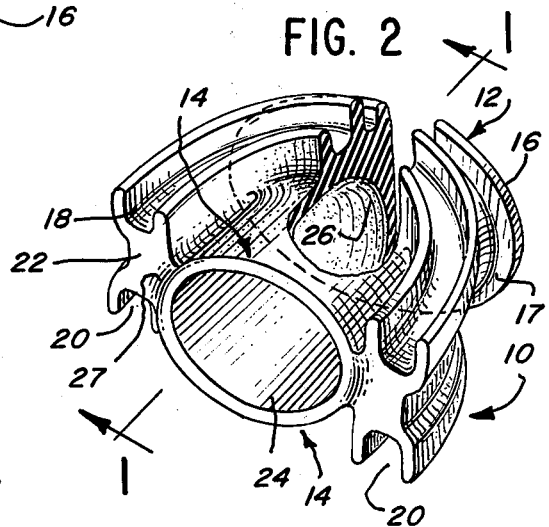
FIG. 2 is a perspective view of the embodiment of the invention shown in FIG. 1, the embodiment including upper and lower dental engaging arches in the anti-snoring device, and with a forward portion of the device partially cut away to provide illustration of the invention's features.

Referring now to the drawings, the anti-snoring and anti-tooth-grinding device of this invention is shown generally as 10 in FIGS. 1 and 2. The device comprises a means 12 for preventing the flow of air through the mouth and an elongated tongue-receiving socket 14 for opening the nasal breathing passage.

FIG. 1 depicts the usual anatomical structure of the mouth of a user of the device of the present invention. The mouth includes an upper jaw 50, a lower jaw 52, a tongue 54, the soft palate or musculus uvulae 56 hanging downwardly approximate the base of the tongue, the posterior pharyngeal wall 57, and the upper and lower dental arches comprising upper and lower gums or upper and lower natural teeth 58 and 60.

Although the drawings depict a device adapted for mounting about the teeth of a user, it should be apparent that the device is readily modifiable for use by people having few if any natural teeth. For such usage, the U-shaped trough is widened so as to fit the upper and/or lower gums of the dental arches.

The body means 12 includes an enlarged and rearwardly curved front plate 16 adapted to be placed over the exterior surface of the lips so as to completely cover the mouth opening. Also formed as part of the body means 12 is an upper U-shaped trough 18 and a lower U-shaped trough 20 molded to closely conform to the configuration of the upper and lower dental arches and adapted to receive either the gums or the natural teeth 58 and 60 of a user. The upper and lower teeth/gum-receiving, U-shaped, troughs 18 and 20 are spaced apart by a central web 22. Both troughs 18 and 20 and the web 22 are generally semicircular in shape to substantially conform to the anatomical shape of the upper and lower dental arches.

The tongue-receiving socket 14 is an elongated element molded integrally with the body means so as to form an oppositely disposed, closed end 26 extending from the rear wall 17 of the curved plate 16 and an open end 24 extending internally of the mouth and sized to accept the tongue of a user therein. As seen in FIG. 2, the socket 14 may be stabilized by diametrically arranged molded portions 27 extending between the exterior of socket 14 and adjacent exterior portions of an arch 18 or web 22.

Figure 3:
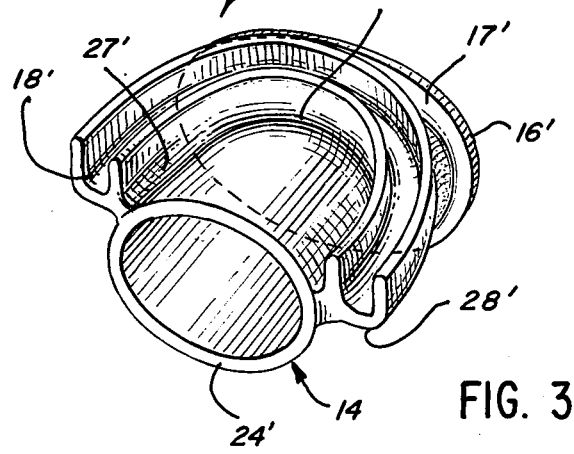
FIG. 3 is a perspective view of a second embodiment of an anti-snoring device of the present invention, the embodiment including an upper dental arch securing trough.

FIG. 3 represents a simplified embodiment 10' of the anti-snoring and anti-bruxism device of the present invention wherein identical numbers represent substantially identical parts of the FIGS. 1-2 embodiment. A tongue-receiving socket 14' is molded integrally with an upper U-shaped trough 18' and a curved front plate 16'. The socket 14' includes a forward, closed end 26' and an open, rear end 24'. In this form, the device 10' may be inserted into the mouth of a user to engage the upper dental arch with the lower surface 28' of the trough resting upon the top of the lower dental arch. The lower trough surface 28' assists in clamping the device 10' between the upper and lower jaws so that the socket 14' will be positioned to hold the tongue 54 forward of its normal position. The main securing force is furnished by the close conformity between the molded upper trough 18' and the upper gum or teeth 58 forming the upper dental arch.

This embodiment permits some voluntary movement of the lower jaw 52 relative to the upper jaw 50 so as to allow swallowing of accumulated saliva. Further, the rigid constraints of the double trough embodiment are absent, thereby alleviating the anxiety which complete enclosure might cause some people. After experiencing this less restrictive model, the user may wish to acquire the more inclusive double trough device 10 or even proceed to a custom-built model.

Although the device could best be fitted by a dentist trained in the art of fabricating similar oral prostheses for the replacement of natural dental structures, a similar device could be produced in several sizes and shapes for over-the-counter sales at considerably less expense. An exact reproduction is not necessary, given the adaptability of the soft and yielding tongue to accommodate itself to a space provided for it.

Figure 4:
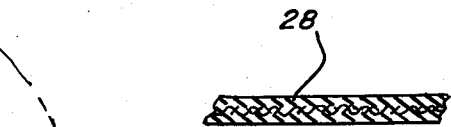
FIG. 4 is a cross-sectional view of a portion of the molded plastic wall of the anti-snoring device illustrating the use of an embedded layer of wire mesh for strength and shape maintenance.

The device is preferably molded of any well-known synthetic plastic resin that displays properties that render the plastic more pliable if warmed to a relatively low temperature above body temperature, with solidification occurring as it cools to body temperature. Alternatively, the troughs could be lined with a yielding rubber or plastic material so that biting down would provide sufficient gripping power to securely hold the device. If desired, an oxidation-resistant wire mesh 28 may be embedded within the plastic resin for enhancing structural strength, rigidity and durability (see FIG. 4).

It should be appreciated that a single troughed design for engaging the lower dental arch is also within the scope of this invention.

OPERATION

In use, the device 10 is placed in hot water or otherwise warmed to a temperature above body temperature wherein the plastic becomes pliable, but which will not burn or otherwise harm the oral tissue which it later is to contact. The device 10 is then positioned in the mouth of the user such that the upper U-shaped trough 18 receives the upper teeth 58 and the lower U-shaped trough 20 receives the lower teeth 60. The user, by closing his jaws, bites into the trought 18 and 20. Since the device is in its heated, pliable state, the upper and lower teeth 58 and 60 make impressions in the trough surfaces 18 and 20. The device 10 is left in position in the mouth until cooling brings about solidification after which the molded impressions operate to secure the device in operative position as seen in FIG. 1.

By means of insertion of the tongue tip and gentle suction therepast, the forward end of the tongue 54 will be drawn into the socket 14 in a substantially airtight relation, so as to be held forward of its normal resting position, thus bringing the body of the tongue also forward from its usual proximity to the soft palate 56 and the posterior pharyngeal wall 57. The front plate 16 and the upper and lower troughs 18 and 20 serve to prevent the oral flow of air, while the socket 14, by maintaining the tongue in a forward position, opens the nasal breathing passageway, which prevents soft tissue vibration as air passes through said passage. By restricting the jaw movement, nocturnal tooth grinding is also prevented.

The single troughed device 10' is substantially identical in operation to the double troughed device 10, the principal difference being that complete jaw movement is not prevented. However, oral breathing is still substantially eliminated by the curved plate 16' overlying the lips, and the single tooth-engaging trough 18' is sufficient to prevent nocturnal tooth grinding.

While one form of the invention has been described, it will be understood that the invention may be utilized in other forms and environments so that the purpose of the appended claims is to cover all such forms of devices not disclosed but which embody the invention disclosed herein.

What is claimed and desired to be secured by Letters Patent of the United States is:

1. An anti-snoring and anti-bruxism device comprising, in combination:
imperforate air flow preventing means of a size and shape to be positioned outwardly of and in overlying relation to a user's lips, for preventing the flow of air through the mouth of a user, and tongue engageable means of a size and shape to be removably positioned in the mouth and when so positioned to hold said imperforate means in operative position overlying the user's lips, said tongue engaging means including an elongated socket means connected to the imperforate air flow preventing means, the socket means having a forward closed end and a rearward open end, the closed end connecting to the air flow preventing means centrally thereof and the open end being of a size, shape and location for receiving a portion of the tongue of a user thereinto to effect an airtight seal therewith when air has been sucked from the socket means past the tongue, such that negative pressure, created by the suction, will serve to hold the portion of the tongue in the socket, whereby the tongue is then held forwardly of its usual resting position behind the lower teeth, thereby bringing the remainder of the body of the tongue forward from its normal proximity to the soft palate, the uvula and the posterior pharyngeal wall, to form and maintain an airway of increased size through the nasopharynx and the oro-pharynx that prevents snoring.

2. A device as in claim 1 including at least one channel-shaped arch, integral with the socket means, and of a size and shape for cooperative reception thereinto of an arch portion of one of the jaws of the user to provide means within the mouth for holding the device in position through the jaw of the user.

3. The device of claim 1 wherein the air flow prevention means includes at least one teeth/gum receiving, U-shaped, trough for removably securing the device in the mouth of a user.

4. A device of claim 3 wherein the flow prevention means includes upper and lower U-shaped troughs for receiving therein the upper and lower teeth or gums of a user.

5. The device of claim 1 wherein the air flow prevention means and the socket means are an integral body molded from a plastic material.

6. The device of claim 5 wherein the plastic material includes embedded reinforcement means spaced between the exterior surfaces of the body of plastic to provide reinforcement, strength and durability.

7. The device of claim 6 wherein the reinforcement means is a wire-like mesh of a non-oxidizing material.

* * * * *